United States Patent
Nguyen (10) Patent No.: US 11,992,232 B2
(45) Date of Patent: May 28, 2024

(54) SYSTEM FOR TREATING THROMBUS IN BODY LUMENS

(71) Applicant: Shockwave Medical, Inc., Santa Clara, CA (US)

(72) Inventor: Hoa Nguyen, Santa Clara, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 182 days.

(21) Appl. No.: 17/477,483

(22) Filed: Sep. 16, 2021

(65) Prior Publication Data
US 2022/0125453 A1  Apr. 28, 2022

Related U.S. Application Data

(60) Provisional application No. 63/106,275, filed on Oct. 27, 2020.

(51) Int. Cl.
*A61B 17/22* (2006.01)

(52) U.S. Cl.
CPC .......... *A61B 17/22012* (2013.01); *A61B 2017/22007* (2013.01); *A61B 2017/22021* (2013.01); *A61B 2017/22079* (2013.01)

(58) Field of Classification Search
CPC  A61B 2017/22007; A61B 2017/22021; A61B 17/22012; A61B 2017/22008; A61B 2017/22079
See application file for complete search history.

(56) References Cited

U.S. PATENT DOCUMENTS

| | | |
|---|---|---|
| 2,916,647 A | 12/1959 | George |
| 3,051,862 A | 8/1962 | Hoff |
| 3,412,288 A | 11/1968 | Ostrander |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

21 C.F.R. 870.5100 Title 21, vol. 8 Apr. 1, 2018 pp. 1-2.

(Continued)

*Primary Examiner* — Todd J Scherbel
(74) *Attorney, Agent, or Firm* — Morrison & Foerster LLP (57) ABSTRACT

The present disclosure relates generally to thrombectomy devices. An exemplary catheter comprises: a central tube; an emitter assembly mounted over the central tube, wherein the emitter assembly comprises: a conductive sheath; a first insulated wire having a first curved distal portion; and a second insulated wire having a second curved distal portion, wherein the first curved distal portion and the second curved distal portion are positioned within the conductive sheath, and wherein the emitter assembly is configured to generate a plurality of cavitation bubbles or shockwaves when a pulsed voltage is applied to the emitter assembly; and an outer tube housing the emitter assembly, wherein the outer tube is configured to receive a conductive fluid, wherein the outer tube comprises a distal opening for releasing the plurality of cavitation bubbles or shockwaves and the conductive fluid in a forward direction to treat thrombus at a treatment site.

22 Claims, 3 Drawing Sheets

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,870,953 A | 10/1989 | DonMicheal et al. |
| 4,878,495 A | 11/1989 | Grayzel |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,556 A | 4/1992 | Filip et al. |
| 5,103,804 A | 4/1992 | Abele et al. |
| 5,116,227 A | 5/1992 | Levy |
| 5,125,928 A | 6/1992 | Parins et al. |
| 5,150,717 A | 9/1992 | Rosen et al. |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,697,281 A | 12/1997 | Eggers et al. |
| 5,709,676 A | 1/1998 | Alt |
| 5,735,811 A | 4/1998 | Brisken |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,404 B1 | 4/2001 | Shadduck |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,855,123 B2 | 2/2005 | Nita |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,856,371 B2 | 10/2014 | Kariti et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,730,715 B2 | 8/2017 | Adams |
| 9,993,292 B2 | 6/2018 | Adams et al. |
| 9,999,788 B2 | 6/2018 | Gattiker et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |
| 10,517,620 B2 | 12/2019 | Adams |

(56) References Cited

U.S. PATENT DOCUMENTS

| | | |
|---|---|---|
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,765,440 B2 | 9/2020 | Tozzi |
| 10,959,743 B2 | 3/2021 | Adams et al. |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 | 10/2022 | Nguyen |
| 11,534,187 B2 | 12/2022 | Bonutti |
| 11,596,423 B2 | 3/2023 | Nguyen et al. |
| 11,596,424 B2 | 3/2023 | Hakala et al. |
| 11,622,780 B2 | 4/2023 | Nguyen et al. |
| 11,696,799 B2 | 7/2023 | Adams et al. |
| 2001/0044596 A1 | 11/2001 | Jaafar |
| 2002/0045890 A1 | 4/2002 | Celliers et al. |
| 2002/0077643 A1 | 6/2002 | Rabiner et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0088262 A1 | 5/2003 | Bonnette et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0193046 A1 | 9/2004 | Nash et al. |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0085054 A1 | 4/2006 | Zikorus et al. |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0149966 A1 | 6/2007 | Dahla et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0177085 A1 | 7/2009 | Maxwell et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0221013 A1 | 8/2012 | Hawkins et al. |
| 2012/0253358 A1 | 10/2012 | Golan et al. |
| 2013/0030431 A1 | 1/2013 | Adams |
| 2013/0030447 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0158453 A1 | 6/2013 | Brouillette et al. |
| 2013/0253622 A1 | 9/2013 | Hooven |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0155830 A1* | 6/2014 | Bonnette ......... A61M 25/0026 604/150 |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0073430 A1 | 3/2015 | Hakala et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2016/0151081 A1 | 6/2016 | Adams et al. |
| 2016/0183957 A1 | 6/2016 | Hakala et al. |
| 2016/0184570 A1 | 6/2016 | Grace et al. |
| 2016/0324534 A1 | 11/2016 | Hawkins et al. |
| 2016/0331389 A1 | 11/2016 | Hakala et al. |
| 2017/0135709 A1 | 5/2017 | Nguyen et al. |
| 2017/0231649 A1 | 8/2017 | Rabiner et al. |
| 2017/0258523 A1* | 9/2017 | Adams ............... A61B 18/00 |
| 2017/0311965 A1 | 11/2017 | Adams |
| 2018/0098779 A1 | 4/2018 | Betelia et al. |
| 2018/0360482 A1 | 12/2018 | Nguyen |
| 2019/0069916 A1 | 3/2019 | Hawkins et al. |
| 2019/0150960 A1 | 5/2019 | Nguyen et al. |
| 2019/0254692 A1 | 8/2019 | Hakala et al. |
| 2019/0388110 A1 | 12/2019 | Nguyen et al. |
| 2020/0085458 A1 | 3/2020 | Nguyen et al. |
| 2020/0383724 A1 | 12/2020 | Adams et al. |
| 2021/0007760 A1* | 1/2021 | Reisin ............ A61B 17/3207 |
| 2021/0085348 A1 | 3/2021 | Nguyen et al. |
| 2021/0085383 A1 | 3/2021 | Vo et al. |
| 2021/0282792 A1 | 9/2021 | Adams et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0011207 A1 | 1/2023 | Nguyen |
| 2023/0043475 A1 | 2/2023 | Adams |
| 2023/0181203 A1 | 6/2023 | Nguyen et al. |

(56) References Cited

U.S. PATENT DOCUMENTS

FOREIGN PATENT DOCUMENTS

| CA | 2104414 | A1 | 2/1995 |
|---|---|---|---|
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| DE | 3038445 | A1 | 5/1982 |
| DE | 202006014285 | U1 | 12/2006 |
| EP | 442199 | A2 | 8/1991 |
| EP | 571306 | A1 | 11/1993 |
| EP | 623360 | A1 | 11/1994 |
| EP | 647435 | A1 | 4/1995 |
| EP | 2253884 | A1 | 11/2010 |
| EP | 2359764 | A1 | 8/2011 |
| EP | 2362798 | B1 | 4/2014 |
| JP | S58-032754 | A | 2/1983 |
| JP | 60-191353 | U | 12/1985 |
| JP | 62-99210 | U | 6/1987 |
| JP | S62275446 | A | 11/1987 |
| JP | 3-63059 | A | 3/1991 |
| JP | H06125915 | A | 5/1994 |
| JP | H0747135 | A | 2/1995 |
| JP | 8-89511 | A | 4/1996 |
| JP | H1099444 | A | 4/1998 |
| JP | 10-314177 | A | 12/1998 |
| JP | 10-513379 | A | 12/1998 |
| JP | 2002-538932 | A | 11/2002 |
| JP | 2004-081374 | A | 3/2004 |
| JP | 2004-357792 | A | 12/2004 |
| JP | 2005-501597 | A | 1/2005 |
| JP | 2005-095410 | A | 4/2005 |
| JP | 2005-515825 | A | 6/2005 |
| JP | 2006-516465 | A | 7/2006 |
| JP | 2007-532182 | A | 11/2007 |
| JP | 2007289707 | A | 11/2007 |
| JP | 2008-506447 | A | 3/2008 |
| JP | 2011-513694 | A | 4/2011 |
| JP | 2011-520248 | A | 7/2011 |
| JP | 2011-524203 | A | 9/2011 |
| JP | 2011-528963 | A | 12/2011 |
| JP | 2012-505050 | A | 3/2012 |
| JP | 2012-508042 | A | 4/2012 |
| JP | 2015522344 | A | 8/2015 |
| JP | 2015525657 | A | 9/2015 |
| JP | 2015528327 | A | 9/2015 |
| JP | 2016508851 | A | 3/2016 |
| JP | 6029828 | B2 | 11/2016 |
| JP | 6081510 | B2 | 2/2017 |
| WO | WO-1989011307 | A1 | 11/1989 |
| WO | WO-1992003975 | A1 | 3/1992 |
| WO | WO-1996024297 | A1 | 8/1996 |
| WO | WO-1999000060 | A1 | 1/1999 |
| WO | WO-1999002096 | A1 | 1/1999 |
| WO | WO-2000051502 | A1 | 9/2000 |
| WO | WO-2000056237 | A2 | 9/2000 |
| WO | WO-2004069072 | A2 | 8/2004 |
| WO | WO-2005034793 | A2 | 4/2005 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010014515 | A3 | 8/2010 |
| WO | WO-2010054048 | A3 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2016109739 | A1 | 7/2016 |
| WO | WO-2018067656 | A1 | 4/2018 |
| WO | WO-2019152898 | A1 * | 8/2019 ......... A61B 17/2202 |

OTHER PUBLICATIONS

Advisory Action received for U.S. Appl. No. 13/615,107, dated Nov. 6, 2015, 3 pages.
Advisory Action Received for U.S. Appl. No. 12/482,995, dated Jun. 2, 2014, 3 pages.
Advisory Action Received for U.S. Appl. No. 12/482,995, dated Sep. 29, 2011, 2 pages.
Advisory Action Received for U.S. Appl. No. 12/581,295, dated Jul. 3, 2014, 3 pages.
Advisory Action Received for U.S. Appl. No. 13/049,199, dated Jun. 7, 2012, 3 pages.
Advisory Action received for U.S. Appl. No. 13/267,383, dated Jan. 6, 2014, 4 pages.
After Orbital Atherectomy Video (post treatment) Video 2019.
Amendment After Final Action received for U.S. Appl. No. 12/482,995, filed May 16, 2014, 8 pages.
Amendment in Response to Non-Final Office Action received for U.S. Appl. No. 12/482,995, filed Jan. 9, 2014 Jan. 9, 2014, 9 pages.
Amighi et al., (2005). "Impact of the Rapid-Exchange Versus Over-the-Wire Technique on Procedural Complications of Renal Artery Angioplasty," J Endovasc Ther., 12:233-239.
Armstrong, Ehrin Responses to Question 6 by Patent Owner's Declarants Ehrin Armstrong, Jan. 29, 2020, 5 pages.
Armstrong, Ehrin Responses to Questions 1-5 by Patent Owner's Declarants Ehrin Armstrong, Jan. 24, 2020, 4 pages.
Athanasoulis, (1980). "Percutaneous Transluminal Angioplasty: General Principles," American journal of Roentgenology, 135:893-900.
Bank of America Merrill Lynch A Simple Solution to a Difficult (and Large) Problem—Initiating Coverage of SWAV Shockwave Medical Inc., Apr. 1, 2019, pp. 1-22.
Becker et al., (1988). "Radiofrequency Balloon Angioplasty," Rationale and Proof of Principle Investigative Radiology, 23(11):810-817.
Before Orbital Aterectomy Video (pre-treatment) Video 2019.
Ben-Dor et al., "Handbook of Shock Waves", Shockwave Medical, Inc. Patent Owner Exhibit 2223, vol. 2, 2001, 824 pages.
Bittl et al., (1993). "Coronary Artery Perforation during Excimer Laser Coronary Angioplasty," Journal of the American College of Cardiology, 21(5):1158-1165.
Bittl et al., (1993). "Publication Information—Coronary Artery Perforation during Excimer Laser Coronary Angioplasty," Journal of the American College of Cardiology, 21(5): 1-6.
Bom et al., (1988). "Intra-Arterial Ultrasonic Imaging for Recanalization by Spark Erosion," Ultrasound in Medicine & Biology,14(4):257-261.
Brinton et al., (2016). "Publication Information—TCT-777 Safety and Performance of the Shockwave Medical Lithoplasty® System in Treating Calcified Peripheral Vascular Lesions: 6-Month Results from the Two-Phase DISRUPT PAD Study," Journal of the American College of Cardiology, 68(18):1-5.
Brinton et al., (2016). "TCT-777 Safety and Performance of the Shockwave Medical Lithoplasty® System in Treating Calcified Peripheral Vascular Lesions: 6-Month Results from the Two-Phase DISRUPT PAD Study," Journal of the American College of Cardiology, 68(18):B314.
Brodmann et al., (2018). "Primary outcomes and mechanism of action of intravascular lithotripsy in calcified femoropopliteal lesions: Results of the Disrupt PAD II," Catheter Cardiovasc Interv., 93(2):335-342.

(56) References Cited

OTHER PUBLICATIONS

Calcium in the Peripheral and Coronary Arteries: The Pathologist View, Deposition Exhibit from Deposition of Dr. Finn, Mar. 6, 2020, 27 pages.
Canfield et al., (2018). "40 Years of Percutaneous Coronary Intervention: History and Future Directions," Journal of Personalized Medicine, 8(33):1-9.
Cardiology Today's Intervention Shockwave Attracts Additional Investment from Abiomed, has IPO Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo> Mar. 12, 2019, pp. 1-2.
Chart of Mantell Detailed Mapping of Provisional to '371 Claims Case No. IPR2019-00405 2020, 12 pages.
Cleveland et al., (2012). "Chapter 38: The Physics of Shock Wave Lithotripsy," Extracorporeal Shock Wave Lithotripsy, 4:317-332.
Concise Description of Relevance Accompanying Third Party Preissuance Submission Under 37 CFR 1.290 for U.S. Appl. No. 15/817,073, filed Aug. 5, 2019, 31 pages.
Connors et al., (2003). "Renal Nerves Mediate Changes in Contralateral Renal Blood Flow after Extracorporeal Shockwave Lithotripsy," Nephron Physiol, 95:67-75.
Das et al., (2014). "Technique Optimization of Orbital Atherectomy in Calcified Peripheral Lesions of the Lower Extremities," Catheterization and Cardiov Interv, 83:115-122.
Deagon, Brian Technology—Shockwave Medical IPO Soars on First Day of Trading Investor's Business Daily, Available Online at <https://www.investors.com/news/technology/shockwave-medical-ipo-soars-trading/> Mar. 7, 2019, pp. 1-15.
Decision Instituting Inter Partes Review for U.S. Pat. No. 8,956,371, by the Patent Trial and Appeal Board dated Jul. 9, 2019, 28 pages.
Decision of Appeals Notice received for Japanese Patent Application No. 2011-534914, mailed on Oct. 17, 2016, 4 pages.
Decision to Grant received for European Patent Application No. 13756766.5, dated May 27, 2016, 2 pages.
Decision to Grant received for European Patent Application No. 09763640.1, dated Feb. 22, 2018, 2 pages.
Decision to Grant received for European Patent Application No. 09825393.3, dated Mar. 13, 2014, 2 pages.
Decision to Grant received for Japanese Patent Application No. 2011-513694, dated Oct. 7, 2014, 3 pages (Official Copy Only) (See Communication under 37 CFR § 1.98(a) (3)).
Declaration and CV of Aloke V. Finn Case IPR2019-00405 Feb. 20, 2020, 45 pages.
Declaration and CV of Jeffrey Chambers Case IPR2019-00405 Dec. 19, 2020, 32 pages.
Declaration of Dr. Morten Olgaard Jensen dated Dec. 6, 2018, pp. 1-137.
Declaration of Juanita DeLoach Exhibit 1236, Case IPR2019-00408 Feb. 18, 2020, 4 pages.
Declaration of Natalie J. Grace dated Apr. 10, 2019, pp. 1-3.
Deposition Exhibit from Deposition of Dr. Jensen, Balloon Attributes that Impact Deliverability, Mar. 4, 2020, 1 page.
Deposition Exhibit from Deposition of Dr. Jensen, Diagram from Wikipedia Page for Balloon Catheters, Mar. 4, 2020, 1 page.
Deposition Exhibit from Deposition of Dr. Jensen, Figures 1 and 2 of JP Patent No. 62-275446 (color added), Mar. 4, 2020, 1 page.
Deposition Exhibit from Deposition of Dr. Jensen, Handwritten Diagram, Mar. 4, 2020, 1 page.
Deposition Exhibit of Ronald David Berger Case No. IPR2019-00405 Jan. 27, 2020, 42 pages.
Deposition Transcript (compressed) of Dr. Aloke Finn, Case No. IPR2019-00405, Mar. 6, 2020, 31 pages.
Deposition Transcript (compressed) of Dr. Daniel van der Weide, Case No. IPR2019-00409, U.S. Pat. No. 8,728,091 B2, Jan. 10, 2020., 111 pages.
Deposition Transcript (compressed) of Dr. Jeffrey Chambers, Case No. IPR2019-00405, Mar. 2, 2020., 81 pages.
Deposition Transcript (compressed) of Dr. Morten Olgaard Jensen, Case No. IPR2019-00405, U.S. Pat. No. 8,956,371, Mar. 4, 2020, 73 pages.
Deposition Transcript (compressed) of Dr. Morten Olgaard Jensen, Case No. IPR2019-00408, U.S. Pat. No. 9,642,673, Feb. 26, 2020., 80 pages.
Deposition Transcript (compressed) of Ronald David Berger Case No. IPR2019-00405 Jan. 27, 2020, 103 pages.
Dewhirst et al., (2003). "Basic Principles of Thermal Dosimetry and Thermal Thresholds for Tissue Damage from Hyperthermia International," Journal of Hyperthermia, 19(3):267-294.
Dewhirst et al., (2003). "Publication Information—Basic Principles of Thermal Dosimetry and Thermal Thresholds for Tissue Damage from Hyperthermia," International Journal of Hyperthermia, 19(3):1-3.
Diamondback 360® Peripheral Orbital Atherectomy System, Cardiovascular Systems, Inc., Patent Owner Exhibit 2231, 2019, 58 pages.
Dictionary.com Definition of 'Angioplasty' Available Online at <https://www.dictionary.com/browse/angioplasty> pp. 1-5.
Dodd, (1842). "Two Cases of Calculus in the Bladder, in Which Lithotripsy Was Performed," Provincial Medical & Surgical Journal, 3(71):368-370.
Dodge Jr., et al., (1992). "Lumen Diameter of Normal Human Coronary Arteries," Influence of Age, Sex, Anatomic Variation, and Left Ventricular Hypertrophy or Dilation Circulation, 86(1):232-246.
E-mail from Cook Alciati to Mark Nelson confirming Dr. Chamber's total compensation amount from Cardiovascular Systems, Inc, *CSI* v. *Shockwave*—Dr. Chambers Testimony, Mar. 20, 2020, 1 page.
Extended European Search Report (includes Supplementary European Search Report and Search Opinion) received for European Patent Application No. 09763640.1, dated Oct. 10, 2013, 5 pages.
Extended European Search Report and Search Opinion received for European Patent Application No. 09825393.3, dated Feb. 28, 2013, 6 pages.
Extended European Search Report received for European Patent Application No. 13827971.6, dated Apr. 12, 2016, 8 pages.
Farb et al., (2002). "Morphological Predictors of Restenosis After Coronary Stenting in Humans," Circulation, pp. 2974-2980.
FDA Clears Lithoplasty Balloon That Shatters Calcified Lesions With Ultrasound Diagnostic and Interventional Cardiology, Available Online at <https://www.dicardiology.com/product/fda-clearslithoplasty-balloon-shatters-calcified-lesions-ultrasound> Sep. 16, 2016, pp. 1-5.
Fernandes et al., (2007). "Enhanced infarct border zone function and altered mechanical activation predict inducibility of monomorphic ventricular tachycardia in patients with ischemic cardiomyopathy," Radiology, 245(3):712-719.
File History of U.S. Pat. No. 8,956,371, pp. 1-1561.
Final Office Action received for U.S. Appl. No. 12/482,995, dated Jul. 22, 2011, 14 pages.
Final Office Action received for U.S. Appl. No. 12/501,619, dated Feb. 21, 2012, 12 pages.
Final Office Action received for U.S. Appl. No. 12/611,997, dated Dec. 11, 2012, 9 pages.
Final Office Action received for U.S. Appl. No. 12/611,997, dated Nov. 10, 2011, 15 pages.
Final Office Action received for U.S. Appl. No. 13/049,199, dated Apr. 4, 2012, 10 pages.
Final Office Action received for U.S. Appl. No. 13/207,381, dated Nov. 2, 2012, 7 pages.
Final Office Action received for U.S. Appl. No. 14/271,342 dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 12/611,997, dated Oct. 24, 2013, 10 pages.
Final Office Action received for U.S. Appl. No. 13/049,199 dated Aug. 11, 2014, 8 pages.

(56) References Cited

OTHER PUBLICATIONS

Final Office Action received for U.S. Appl. No. 13/207,381, dated Nov. 7, 2013, 7 pages.
Final Office Action Received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107 dated Sep. 1, 2015, 9 pages.
Final Office Action received for U.S. Appl. No. 13/646,570, dated Dec. 23, 2014, 10 pages.
Final Office Action received for U.S. Appl. No. 14/229,735, dated Aug. 27, 2015, 7 pages.
Final Office Action received for U.S. Appl. No. 14/273,063, dated Dec. 28, 2016, 11 pages.
Final Office Action received for U.S. Appl. No. 15/213,105, dated May 4, 2018, 8 pages.
Final Office Action received for U.S. Appl. No. 14/660,539, dated Aug. 3, 2017, 11 pages.
Final Written Decision *Ariosa Diagnostics Inc.* vs. *Illumina Inc.* dated Jan. 7, 2016, pp. 1-18.
Final Written Decision for U.S. Pat. No. 8,956,371, by the Patent Trial and Appeal Board dated Jul. 8, 2020, 89 pages.
Fung, Y. C. Biomechanics—Mechanical Properties of Living Tissues Second Edition, Springer 1993, 14 pages.
Gambihler et al., (1994). "Permeabilization of the Plasma Membrane of LI210 Mouse Leukemia Cells Using Lithotripter Shock Waves," The Journal of Membrane Biology, 141:267-275.
Gottlieb,, Scott U.S. Department of Health and Human Services, Food and Drug Administration Report to Congress by Scott Gottlieb Exhibit 1217 Sep. 30, 2018, 10 pages.
Grassi et al., (2012). "Novel Antihypertensive Therapies: Renal Sympathetic Nerve Ablation and Carotid Baroreceptor Stimulation," Curr Hypertens Rep, 14:567-572.
Grocela et al., (1997). "Intracorporeal Lithotripsy," Instrumentation and Development Urologic Clinics of North America, 24(1):13-23.
Hawkins, et al. U.S. Appl. No. 61/061,170, filed Jun. 13, 2008, titled "Shockwave Balloon Catheter System".
Hill, Jonathan M., Deposition Transcript (compressed) of Jonathan M. Hill, M.D. Exhibit 1211, Case No. IPR2019-00408, U.S. Pat. No. 9,642,673 Dec. 16, 2019, 63 pages.
Hodges et al., (1994). "Publication Information—Ultrasound Determination of Total Arterial Wall Thickness," Journal of Vascular Surgery, 19(4):1-13.
Hodges et al., (1994). "Ultrasound Determination of Total Arterial Wall Thickness," Journal of Vascular Surgery, 19(4):745-753.
Huang et al., (1998). "Cost Effectiveness of Electrohydraulic Lithotripsy v Candela Pulsed-Dye Laser in Management of the Distal Ureteral Stone," Journal of Endourology, 12(3):237-240.
Intention to Grant received for European Patent Application No. 09763640.1, dated Oct. 11, 2017, 8 pages.
Intention to Grant received for European Patent Application No. 13756766.5, dated Jan. 8, 2016, 5 pages.
Intention to Grant received for European Patent Application No. 13827971.6, dated Sep. 28, 2018, 8 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2009/063354, dated May 19, 2011, 6 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2012/063925, dated May 22, 2014, 12 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987 dated Nov. 20, 2014, 11 pages.
International Preliminary Report on Patentability received for PCT Patent Application No. PCT/US2013/048277 dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533 dated Mar. 26, 2015, 10 pages.
International Preliminary Report on Patentability received for PCT Patent Application No. PCT/US2015/029088, dated Nov. 17, 2016, 8 pages.
International Preliminary Report on Patentability received for PCT Patent Application No. PCT/US2016/060817, dated May 31, 2018, 9 pages.
International Preliminary Report on Patentability received for PCT Patent Application No. PCT/US2018/059083, dated May 28, 2020, 6 pages.
International Preliminary Report on Patentability received for PCT Patent Application No. PCT/US2019/035750, dated Dec. 30, 2020, 11 pages.
International Search Report and Written Opinion Received for PCT Application No. PCT/US2018/034855 , dated Aug. 23, 2018, 13 pages.
International Search Report and Written Opinion Received for PCT Application No. PCT/US2018/059083, dated Jan. 22, 2019, 8 pages.
International Search Report and Written Opinion received for PCT Patent Application No. PCT/US2013/031805 dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088 dated Jul. 16, 2015, 13 pages.
International Search Report and Written Opinion received for PCT Patent Application No. PCT/US2016/060817, dated Feb. 20, 2017, 13 pages.
International Search Report and Written Opinion received for PCT Patent Application No. PCT/US2019/035750, dated Aug. 1, 2019, 21 pages.
International Search Report and Written Opinion received for PCT Patent Application No. PCT/US2020/046134, dated Oct. 26, 2020, 18 pages.
International Search Report and Written Opinion received for PCT Patent Application No. PCT/US2020/051551, dated Jan. 11, 2021, 16 pages.
International Search Report received for PCT Patent Application No. PCT/US2009/047070, dated Jan. 19, 2010, 4 pages.
International Search Report received for PCT Patent Application No. PCT/US2009/063354, dated Jun. 11, 2010, 3 pages.
International Search Report received for PCT Patent Application No. PCT/US2012/023172, dated Sep. 28, 2012, 3 pages.
International Written Opinion received for PCT Patent Application No. PCT/US2009/047070, dated Jan. 19, 2010, 5 pages.

(56) References Cited

OTHER PUBLICATIONS

International Written Opinion received for PCT Patent Application No. PCT/US2009/063354, dated Jun. 11, 2010, 4 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
Jahnke et al., (2008). "Retrospective Study of Rapid-Exchange Monorail Versus Over-the-Wire Technique for Femoropopliteal Angioplasty," Cardiovascular and Interventional Radiology, 31:854-859.
Johnston et al., (2004). "Publication Information—Non-Newtonian Blood Flow in Human Right Coronary Arteries: Steady State Simulations," Journal of Biomechanics, 37(5):1-2.
Johnston et al., (2006). "Non-Newtonian Blood Flow in Human Right Coronary Arteries: Transient Simulations," Journal of Biomechanics, 39(6):1-35.
Kaplan et al., (1993). "Healing after Arterial Dilatation with Radiofrequency Thermal and Nonthermal Balloon Angioplasty Systems," Journal of Investigative Surgery, 6:33-52.
Kereiakes, Dean J., Deposition Transcript (compressed) of Dean J. Kereiakes Exhibit 1213, Cases No. 2019-00405, 00408 and 00409 Jan. 7, 2020, 65 pages.
Knuttinen et al., (2014). "Unintended Thermal Injuries from Radiofrequency Ablation: Organ Protection with an Angioplasty Balloon Catheter in an Animal Model," Journal of Clinical Imaging Science, 4(1):1-6.
Kodama et al., (2002). "Shock wave-mediated molecular delivery into cells," Biochimica et Biophysica Acta, 1542:186-194.
Lauer et al., (1997). "Shock wave permeabilization as a new gene transfer method," Gene Therapy, 4:710-715.
Lee et al., (1991). "Structure-Dependent Dynamic Mechanical Behavior of Fibrous Caps From Human Atherosclerotic Plaques," Circulation, 83(5):1764-1770.
Lee et al., (2017). "Orbital atherectomy for treating de novo, severely calcified coronary lesions: 3-year results of the pivotal ORBIT II trial," Cardiovascular Revascularization Medicine, 18:261-264.
Lee et al., (2018). "Acute Procedural Outcomes of Orbital Atherectomy for the Treatment of Profunda Femoris Artery Disease: Subanalysis of the CONFIRM Registries," J Invasive Cardio, 330(5):177-181.
Linnemeier et al., (1993). "Radiation Exposure: Comparison of Rapid Exchange and Conventional Over-the-Wire Coronary Angioplasty Systems," Catheterization and Cardiovascular Diagnosis, 30:11-14.
Lipowski, et al. U.S. Appl. No. 61/051,262 pp. 1-36.
Liu et al., (2015). "Current Understanding of Coronary Artery Calcification," Journal of Geriatric Cardiology, 12:668-675.
Med Device Online Angioplasty Balloons Advanced Polymers Inc., Available Online at <https://www.meddeviceonline.com/doc/angioplasty-balloons-0001>, 1 page.
MedlinePlus Angioplasty U.S. National Library of Medicine, Available Online at <https://medlineplus.gov/angioplasty.html>, pp. 1-4.
Meraj et al., (2018). "Clinical outcomes of Atherectomy Prior to Percutaneous Coronary Intervention: A Comparison of Outcomes following Rotational Versus Orbital Atherectomy (COAP-PCI study)," Journal of Interventional Cardiology, 31:478-485.
Mills et al., (2019). "Cracking the Code on Calcium; Initiate with Buy, $39 Target Canaccord Genuity—Capital Markets," US Equity Research Apr. 1, 2019, pp. 1-63.
Mitomo, "Intravascular lithotripsy: A Novel Technology for Treating Calcified Coronary Stenoses Cardiovascular News," Online Available at <https://cardiovascularnews.com/intravascular-lithotripsy-anovel-technology-for-treating-calcified-coronary-stenoses> Apr. 18, 2018, pp. 1-4.
Mooney et al., (1990). "Monorail Piccolino Catheter: A New Rapid Exchange/Ultralow Profile Coronary Angioplasty System," Catheterization and Cardiovascular Diagnosis, 20:114-119.
Mori et al., "Coronary Artery Calcification and its Progression—What Does it Really Mean", American College of Cardiology Foundation, vol. 11, No. 1, 2018, 16 pages.
Myler et al., (1987). "Recurrence After Coronary Aangioplasty," Catheterization and Cardiovascular Diagnosis, 13:77-86.
Nichols et al., (2005). "McDonald's Blood Flow in Arteries: Theoretical," Experimental and Clinical Principles 5th Edition, pp. 1-9.
Nisonson et al., (1986). "Ambulatory Extracorporeal Shockwave Lithotripsy," Urology, 28(5):381-384.
Non Final Office Action received for U.S. Appl. No. 12/482,995, dated Aug. 13, 2014, 10 pages.
Non Final Office Action received for U.S. Appl. No. 12/482,995, dated Jul. 12, 2013, 11 pages.
Non Final Office Action received for U.S. Appl. No. 12/611,997, dated Nov. 26, 2014, 8 pages.
Non Final Office Action received for U.S. Appl. No. 13/207,381, dated Nov. 25, 2014, 5 pages.
Non Final Office Action received for U.S. Appl. No. 13/465,264, dated Oct. 29, 2014, 13 pages.
Non Final Office Action received for U.S. Appl. No. 13/646,570, dated Oct. 29, 2014, 10 pages.
Non Final Office Action received for U.S. Appl. No. 14/079,463, dated Mar. 4, 2014, 9 pages.
Non Final Office Action received for U.S. Appl. No. 12/482,995, dated Feb. 11, 2011, 27 pages.
Non Final Office Action received for U.S. Appl. No. 12/501,619, dated Nov. 3, 2011, 10 pages.
Non Final Office Action received for U.S. Appl. No. 12/611,997, dated Apr. 8, 2013, 9 pages.
Non Final Office Action received for U.S. Appl. No. 12/611,997, dated Aug. 24, 2012, 11 pages.
Non Final Office Action received for U.S. Appl. No. 12/611,997, dated Jun. 21, 2011, 13 pages.
Non Final Office Action received for U.S. Appl. No. 13/049,199, dated Dec. 12, 2011, 10 pages.
Non Final Office Action received for U.S. Appl. No. 13/207,381, dated Feb. 22, 2013, 7 pages.
Non Final Office Action received for U.S. Appl. No. 13/207,381, dated Jun. 12, 2012, 6 pages.
Non Final Office Action received for U.S. Appl. No. 13/534,658, dated Mar. 11, 2016, 12 pages.
Non Final Office Action received for U.S. Appl. No. 14/218,858, dated Mar. 30, 2016, 13 pages.
Non Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 12/611,997, dated Feb. 13, 2014, 9 pages.
Non-Final Office Action received for U.S. Appl. No. 13/049,199, dated Feb. 4, 2014, 8 pages.
Non-Final Office Action received for U.S. Appl. No. 13/207,381, dated Feb. 25, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 14/273,063, dated Jun. 3, 2016, 9 pages.
Non-Final Office Action received for U.S. Appl. No. 14/660,539, dated Nov. 24, 2017, 10 pages.

(56) References Cited

OTHER PUBLICATIONS

Non-Final Office Action received for U.S. Appl. No. 14/693,155, dated Jan. 15, 2016, 6 pages.
Non-Final Office Action received for U.S. Appl. No. 15/213,105, dated Nov. 28, 2017, 7 pages.
Non-Final Office Action received for U.S. Appl. No. 15/346,132, dated Dec. 20, 2018, 14 pages.
Non-Final Office Action received for U.S. Appl. No. 15/474,885, dated Oct. 5, 2017, 9 pages.
Non-Final Office Action received for U.S. Appl. No. 15/652,070, dated Jan. 11, 2019, 9 pages.
Non-Final Office Action received for U.S. Appl. No. 15/817,073, dated Nov. 12, 2019, 18 pages.
Non-Final Office Action received for U.S. Appl. No. 14/660,539, dated Mar. 6, 2017, 14 pages.
Notice of Acceptance Received for Australian Patent Application No. 2009257368, dated Aug. 28, 2014, 2 pages.
Notice of Acceptance Received for Australian Patent Application No. 2009313507, dated Nov. 17, 2014, 2 pages.
Notice of Acceptance received for Australian Patent Application No. 2013284490, dated May 8, 2018, 3 pages.
Notice of Acceptance received for Australian Patent Application No. 2013300176, dated Aug. 7, 2017, 3 pages.
Notice of Allowance received for Japanese Patent Application No. 2015-520522, dated Feb. 23, 2017. 3 pages of Official Copy Only.
Notice of Allowance received for Canadian Patent Application No. 2,727,429, dated May 26, 2015, 1 page.
Notice of Allowance received for Canadian Patent Application No. 2,779,600, dated Jul. 7, 2017, 1 page.
Notice of Allowance received for Chinese Patent Application No. 201380033808.3, dated Dec. 29, 2016, 4 pages (Official Copy Only).
Notice of Allowance received for Chinese Patent Application No. 201380041656.1, dated Mar. 3, 2017, 4 pages (Official Copy Only).
Notice of Allowance received for Japanese Patent Application No. 2015-036444, dated Jan. 13, 2017, 3 pages (Official Copy Only).
Notice of Allowance received for Japanese Patent Application No. 2015-520522, dated Feb. 23, 2017, 3 pages (Official Copy Only).
Notice of Allowance received for Japanese Patent Application No. 2015-526523, dated Dec. 4, 2017, 3 pages (Official Copy Only) (See Communication under 37 CFR § 1.98(a) (3)).
Notice of Allowance received for Japanese Patent Application No. 2016-143049, dated Nov. 13, 2017, 3 pages (Official copy only).
Notice of Allowance received for Japanese Patent Application No. 2017-212658, dated May 13, 2019, 3 pages (Official Copy Only).
Notice of Allowance received for U.S. Appl. No. 15/652,070, dated May 21, 2019, 8 pages.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 12/611,997, dated Apr. 15, 2015, 7 pages.
Notice of Allowance received for U.S. Appl. No. 13/207,381, dated Apr. 14, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 14/273,063, dated Apr. 12, 2017. 7 pages.
Notice of Allowance received for U.S. Appl. No. 14/660,539, dated Apr. 6, 2018, 7 pages.
Notice of Allowance received for U.S. Appl. No. 14/693,155, dated Apr. 26, 2016, 9 pages.
Notice of Allowance received for U.S. Appl. No. 15/213,105, dated Aug. 10, 2018, 8 pages.
Notice of Allowance received for U.S. Appl. No. 15/220,999, dated Oct. 10, 2018, 10 pages.
Notice of Allowance received for U.S. Appl. No. 15/474,885, dated Feb. 14, 2018, 5 pages.
Notice of Allowance received for U.S. Appl. No. 15/817,073, dated Mar. 13, 2020, 8 pages.
Notice of Allowance received for U.S. Appl. No. 13/615,107, dated Dec. 31, 2015, 10 pages.
Office Action received for Japanese Patent Application No. 2016-143049, dated Jul. 28, 2017, 7 pages (4 pages of English Translation and 3 pages of Official copy).
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2009313507, dated Nov. 13, 2013, 3 pages.
Office Action received for Australian Patent Application No. 2013284490, dated Jun. 5, 2017, 4 pages.
Office Action received for Australian Patent Application No. 2013284490, dated May 3, 2018, 5 pages.
Office Action received for Australian Patent Application No. 2013300176, dated Nov. 10, 2016, 2 pages.
Office Action received for Australian Patent Application No. 2018204691, dated Jul. 12, 2018, 2 pages.
Office Action received for Canadian Patent Application No. 2,727,429, dated Apr. 14, 2015, 4 pages.
Office Action received for Canadian Patent Application No. 2,779,600, dated Jan. 4, 2016, 6 pages.
Office Action received for Canadian Patent Application No. 2,779,600, dated Oct. 19, 2016, 3 pages.
Office Action received for Chinese Patent Application No. 200980153687.X, dated Dec. 26, 2012, 11 pages of Official copy only.
Office Action received for Chinese Patent Application No. 200980153687.X, dated Jul. 11, 2013, 11 pages (Official copy only).
Office Action received for Chinese Patent Application No. 201380033808.3, dated Jul. 5, 2016, 9 pages (3 pages of English translation and 6 pages of Official copy).
Office Action received for Chinese Patent Application No. 201380041656.1, dated Jul. 5, 2016, 9 pages (4 pages of English translation and 5 pages of Official copy).
Office Action received for Chinese Patent Application No. 201380042887.4, dated Aug. 8, 2016, 9 pages (4 pages of English translation and 5 pages of Official copy).

(56) References Cited

OTHER PUBLICATIONS

Office Action received for European Patent Application No. 13735174.8, dated Oct. 15, 2018, 5 pages.
Office Action received for European Patent Application No. 09763640.1, dated Dec. 2, 2016, 4 pages.
Office Action received for Japanese Patent Application No. 2011-513694, dated Aug. 27, 2013, 6 pages (3 pages of English Translation and 3 pages of Official copy).
Office Action Received for Japanese Patent Application No. 2011-513694, dated Jun. 10, 2014, 4 pages total (2 pages of Official Copy and 2 pages of English Translation).
Office Action Received for Japanese Patent Application No. 2011-534914, dated Jan. 13, 2015, 9 pages(7 pages of English Translation and 2 pages of Official Copy.
Office Action Received for Japanese Patent Application No. 2011-534914, dated Jul. 15, 2014, 3 pages (1 page of English Translation and 2 pages of Official Copy).
Office Action received for Japanese Patent Application No. 2011-534914, dated May 10, 2016, 10 pages ( 4 pages of Official Copy and 6 pages of English Translation).
Office Action received for Japanese Patent Application No. 2011-534914, dated Oct. 1, 2013, 5 pages (2 pages of English Translation and 3 pages of Official copy).
Office Action received for Japanese Patent Application No. 2014-158517, dated Feb. 15, 2017, 8 pages (5 pages of English Translation and 3 pages of Official Copy Only).
Office Action Received for Japanese Patent Application No. 2014-158517, dated Jun. 22, 2017. 14 pages of official Copy only.
Office Action Received for Japanese Patent Application No. 2014-158517, dated May 19, 2015, 5 pages (2 pages of English Translation and 3 pages of Official Copy).
Office Action received for Japanese Patent Application No. 2015-036444, dated Feb. 23, 2016, 3 pages of English translation only.
Office Action received for Japanese Patent Application No. 2015-526523, dated Jan. 25, 2017, 8 pages (5 pages of English Translation and 3 pages of Official Copy Only).
Office Action received for Japanese Patent Application No. 2016-143049, dated Apr. 24, 2017. 5 pages ( 2 pages of English Translation and 3 pages of Official copy).
Office Action received for Japanese Patent Application No. 2017-212658, dated Dec. 20, 2018, 10 pages (6 pages of English Translation and 4 pages of Official Copy).
Office Action received for Japanese Patent Application No. 2017-212658, dated Sep. 12, 2018, 8 pages (5 pages of English Translation and 3 pages of Official Copy).
Office Action received for Japanese Patent Application No. 2017-212659, dated Jul. 5, 2018, 2 pages (Official Copy Only).
Office Action received for Japanese Patent Application No. 2017-212659, dated Mar. 4, 2019, 2 pages (Official Copy Only).
Office Action received for Japanese Patent Application No. 2015-036444, dated Sep. 14, 2016, 5 pages (3 Pages of English Translation and 2 Pages of Official Copy).
Office Action received for Japanese Patent Application No. 2016-094326, dated Dec. 2, 2016, 4 pages (2 pages of English Translation and 2 pages Official Copy Only).
Office Action received for Japanese Patent Application No. 2016-094326, dated Jul. 6, 2017, 2 pages (Official Copy Only).
Operator's Manual Intravascular Lithotripsy (IVL) Generator and Connector Cable LBL 61876 Rev. E Mar. 2018, pp. 1-16.
Kini et al., Optical Coherence Tomography Assessment of the Mechanistic Effects of Rotational and Orbital Atherectomy in Severely Calcified Coronary Lesions, Catheterization and Cardiovascular Interventions, vol. 86, 2015, pp. 1024-1032.
Oral Argument *Cardiovascular Systems Inc.* vs. *Shockwave Medical Inc.* in Inter Partes Review No. IPR2019-00405, dated May 8, 2019, 35 pages.
Otsuka et al., "Has Our Understanding of Calcification in Human Coronary Atherosclerosis Progressed", Coronary Calcification, Apr. 2014, pp. 724-738.

Patent Owner Preliminary Response for U.S. Pat. No. 8,956,371, by the Patent Trial and Appeal Board dated Apr. 10, 2019, 79 pages.
Patent Owner Sur-Reply for U.S. Pat. No. 8,956,371, by the Patent Trial and Appeal Board dated May 24, 2019, 8 pages.
Patent Owner's Response dated Nov. 7, 2019, 70 pages.
Patent Owner's Response Case No. IPR2019-00409 dated Nov. 3, 2019, 65 pages.
Patent Owner's Updated Exhibit List for U.S. Pat. No. 8,956,371, by the Patent Trial and Appeal Board dated May 24, 2019, 7 pages.
Patent Owner's Sur-Reply for U.S. Pat. No. 8,956,371, by the Patent Trial and Appeal Board dated Mar. 20, 2020, Mar. 20, 2020, 53 pages.
Patent Owner's Updated Exhibit List for U.S. Pat. No. 8,956,371, by the Patent Trial and Appeal Board dated Mar. 20, 2020, 18 pages.
Patterson et al., (1985). "The Etiology and Treatment of delayed Bleeding following Percutaneous Lithotripsy," The Journal of Urology, 133:447-451.
Peripheral Diamondback 360 Peripheral OAS, Micro Crown, Patents, Cardiovascular Systems, Inc., 201 T, 6 pages.
Peripheral Intravascular Lithotripsy (IVL) Catheter—Instructions for Use (IFU) LBL 61932, Rev A Instructions for Use US Jan. 2018, pp. 1-5.
Peripheral Intravascular Lithotripsy (IVL) Catheter Instructions for Use (IFU) LBL 61959, Rev. B Instructions for Use Jun. 2018, pp. 1-7.
Peripheral IVL Case Setup and Execution Shockwave Medical Inc., Available Online at <http://shockwavemedical.com/wp-content/uploads/2018/12/PAD-IVL-Case-Set-Up.pdf>, pp. 1-11.
Petition for Inter Partes Review for U.S. Pat. No. 8,956,371, issued on Feb. 17, 2015, 75 pages.
Petitioner Power of Attorney for U.S. Pat. No. 8,956,371, dated Dec. 6, 2018, pp. 1-2.
Petitioner's Reply Brief Case IPR2019-00405 Feb. 21, 2020, 65 pages.
Petitioner's Reply to Patent Owner's Preliminary Response for U.S. Pat. No. 8,956,371, by the Patent Trial and Appeal Board dated May 15, 2019, 7 pages.
Press Release: Shockwave Medical Reports Fourth Quarter and Full Year 2019 Financial Results and Provides Full Year 2020 Financial Outlook, Mar. 4, 2020, 7 pages.
Press Release: St. Francis Participates in Landmark Study Using Sonic Pressure Waves to Treat Heart Blockages, Catholic Health, Jan. 17, 2019, 5 pages.
Publicly available Professional & Educational Background Summary for Clifton Alferness Exhibit 1229 2013, 3 pages.
Publicly available Professional & Educational Background Summary for Daniel Hawkins Exhibit 1226, 2018, 2 pages.
Publicly available Professional & Educational Background Summary for Guy Levy Exhibit 1253 2019, 2 pages.
Publicly available Professional & Educational Background Summary for John Adams Exhibit 1221, 2009, 2 pages.
Publicly available Professional & Educational Background Summary for Krishna Bhatta Exhibit 1251 2005, 2 pages.
Publicly available Professional & Educational Background Summary for Marat Izrailevich Lerner 2020, 3 pages.
Publicly available Professional & Educational Background Summary for Marat Lerner 2008-2020, 4 pages.
Publicly available Professional & Educational Background Summary for Naoki Uchiyama 2020, 2 pages.
Publicly available Professional & Educational Background Summary for Ralph de la Torre Exhibit 1252 2010, 2 pages.
Publicly available Professional & Educational Background Summary for Robert Mantell Exhibit 1256 2000, 2 pages.
Publicly available Professional & Educational Background Summary for Stepan Khachin 2008-2020, 3 pages.
Publicly available Professional & Educational Background Summary for Valery Diamant Exhibit 1257 2017, 2 pages.
Redline of Shockwave Provisional to Utility, pp. 1-6.
Response to Final Office Action received for U.S. Appl. No. 12/482,995, filed Sep. 19, 2011 dated Sep. 19, 2011, 20 pages.
Ricks, Delthia Long Island Doctors Using Sound Waves to Loosen Calcium Deposits from Arteries, Restore Blood Flow News/Health, (56) References Cited

OTHER PUBLICATIONS

Available Online at <https://www.newsday.com/news/health/calcium-treatment-st-francis-hospital-1.27314331> Feb. 15, 2019, p. 1-4.
Rocha-Singh, et al. Peripheral Arterial Calcification: Prevalence, Mechanism, Detection, and Clinical Implications Catheterization and Cardiovascular Interventions, vol. 86 2014 pp. E212-E220.
Rosenschein et al., (1992). "Shock-Wave Thrombus Ablation, a New Method for Noninvasive Mechanical Thrombolysis," The American Journal of Cardiology, 70:1358-1361.
Sakes et al., (2016). "Crossing Total Occlusions: Navigating Towards Recanalization," Cardiovascular Engineering and Technology, 7(2):103-117.
Salunke et al., (2001). "Compressive Stress-Relaxation of Human Atherosclerotic Plaque," J Biomed Mater, 55:236-241.
Sasaki et al., (2015). New Insight into Scar-related Ventricular Tachycardia Circuits in Ischemic Cardiomyopathy: Fat Deposition after Myocardial Infarction on Computed Tomography, Heart Rhythm, 12(7):1508-1518.
Schenkman, Noah Ureter Anatomy WebMD LLC, Emedicine.medscape.com, Jul. 10, 2013, 8 pages.
Second Declaration of Natalie J. Grace dated May 24, 2019, pp. 1-2.
Shlofmitz et al., (2019). "Orbital Atherectomy: A Comprehensive Review," Interv Cardiol Clin, 8(2):161-171.
ShockwaveMedical.com Intravascular Lithotripsy (IVL) Available Online at <https://shockwavemedical.com/technology/intravascular-lithotripsy-ivl/?country=Egypt> 2019, pp. 1-4.
Simpson et al., (1962). "A New Catheter System for Coronary Angioplasty," The American Journal of Cardiology, 49:1216-1222.
Smith et al., (1992). "Microwave Thermal Balloon Angioplasty in the Normal Rabbit," American Heart Journal, 123(6):1516-1521.
Sokol (2011). "Clinical Anatomy of the Uterus, Fallopian Tubes, and Ovaries," Glob. Libr. Women's Med., pp. 1-12.
Soukas, "Deposition Transcript (compressed) of Peter Soukas, Cases:—IPR2019-00405, IPR2019-00408, IPR2019-00409," Dec. 30, 2019, 10 pages.
Stephens, William, "Deposition Transcript (compressed) of William Patrick Stephens Case No. IPR2019-00408," Jan. 22, 2020, 55 pages.
Supplemental Declaration of Dr. Morten Olgaard Jensen Case IPR2019-00405 Feb. 21, 2020, 136 pages.
Tanaka et al., (2001). "A New Radiofrequency Thermal Balloon Catheter for Pulmonary Vein Isolation," Journal of the American College of Cardiology, 38(7):2079-2086.
Thiem et al., (2018). "The 12-Month Results of the EffPac Trial," Journal of Vascular Surgery, 68(55):e122-e123.
Third Party Preissuance Submission for U.S. Appl. No. 15/817,073, filed Aug. 5, 2019, 3 pages.
Third Party Preissuance Submission for U.S. Appl. No. 16/436,186, filed Jan. 10, 2020, 3 pages.
Third-Party Submission Under 37 CFR 1.290 Concise Description of Relevance for U.S. Appl. No. 15/817,073, filed Aug. 5, 2019, 3 pages.
Top Cardiovascular Innovation Award Cardiovascular Research Technologies (CRT) 2015, 1 page.
WebMD.com Definition of 'Angioplasty' Available Online at <https://www.webmd.com/heart-disease/heart-failure/qa/what-is-the-definition-of-angioplasty> Oct. 29, 2017, pp. 1-2.
Weide, Daniel Deposition Transcript (compressed) of Daniel van der Weide, Ph.D. Exhibit 1203, Case No. IPR2019-00408, U.S. Pat. No. 9,642,673 B2 Jan. 13, 2020, 94 pages.
Wells Fargo Securities LLC SWAV: Initiating With a Market Perform Rating Shockwave Medical Inc. Apr. 1, 2019, pp. 1-34.
Written Opinion received for PCT Patent Application No. PCT/US2012/023172, dated Sep. 28, 2012, 4 pages.
Written Opinion received for PCT Patent Application No. PCT/US2009/047070, dated Jan. 19, 2010, 5 pages.
Yamamoto et al., (2018). "Effect of orbital atherectomy in calcified coronary artery lesions as assessed by optical coherence tomography," Catheter Cardiovasc Interv, 93(7):1211-1218.
Zhong et al., (1997). "Publication Information—Transient Oscillation of Cavitation Bubbles Near Stone Surface During Electrohydraulic Lithotripsy," Journal of Endourology, 11, 1 page.
Zhong et al., (1997). "Transient Oscillation of Cavitation Bubbles Near Stone Surface During Electrohydraulic Lithotripsy," Journal of Endourology, 11(1):55-61.
Non-Final Office Action received for U.S. Appl. No. 16/436,186, dated Sep. 21, 2021, 16 pages.
International Search Report and Written Opinion received for PCT Patent Application No. PCT/US2021/071938, dated Jan. 18, 2022, 15 pages.
Non-Final Office Action received for U.S. Appl. No. 16/436,186, dated Jun. 10, 2022, 14 pages.
Non-Final Office Action received for U.S. Appl. No. 17/025,866, dated Mar. 2, 2022, 9 pages.
Notice of Allowance received for U.S. Appl. No. 17/025,866, dated Jun. 23, 2022, 8 pages.
Notice of Allowance received for U.S. Appl. No. 17/025,866, dated Jul. 7, 2022, 3 pages.
Notice of Allowance received for U.S. Appl. No. 16/436,186, dated Apr. 22, 2022, 8 pages.
Notice of Allowance received for U.S. Appl. No. 16/436,186, dated Nov. 2, 2022, 7 pages.
Notice of Allowance received for U.S. Appl. No. 16/436,186, dated Nov. 10, 2022, 4 pages.

* cited by examiner

SYSTEM FOR TREATING THROMBUS IN BODY LUMENS

PRIORITY

This application claims priority to U.S. Provisional Patent Application Ser. No. 63/106,275, filed Oct. 27, 2020, the entire disclosure of which is incorporated by reference.

FIELD OF THE DISCLOSURE

The present disclosure relates generally to thrombectomy devices, and more specifically, to thrombectomy devices designed to generate cavitation bubbles and/or shockwaves for reducing or removing thrombus from the vascular system of a patient.

BACKGROUND

Thrombectomy devices are designed to reduce clot burden and partially or completely remove a blood clot (i.e., thrombus) from the vascular system of a patient. Currently, the mechanism of removing thrombus in most thrombectomy devices is mechanical or involves a combination of the plasminogen activator ("tPA") treatment and a mechanical process. Some of these devices use ultrasound for the purpose of diffusing tissue plasminogen activator (tPA). It does this by increasing permeability in thrombus structure, which exposes more sites to which thrombolytic agents can bind. These devices all have deficiencies, as they provide an undesirably slow rate of clot removal, which typically requires an overnight stay in the hospital. Further, these devices tend to be expensive, bulky, and difficult to operate. Further still, these devices can involve a high loss of blood in the patient.

Accordingly, a need exists for a device that treats blood clots without the use of drugs (e.g., tPA) and provides a cost-effective and time-efficient solution for treating thrombus.

BRIEF SUMMARY

The present invention relates to thrombectomy devices designed to generate cavitation bubbles and/or shockwaves for reducing or removing thrombus from the vascular system of a patient. Because embodiments of the present invention do not require the use of drugs (e.g., tPA) and can work quickly (e.g., less than 2 hours), the present invention provides a cost-effective and efficient solution for treating thrombus. Short procedure time can minimize bleeding complication and reduce infection.

An exemplary catheter comprises: a central tube; an emitter assembly mounted over the central tube, wherein the emitter assembly comprises: a conductive sheath; a first insulated wire having a first curved distal portion; and a second insulated wire having a second curved distal portion, wherein the first curved distal portion and the second curved distal portion are positioned within the conductive sheath, and wherein the emitter assembly is configured to generate a plurality of cavitation bubbles or shockwaves when a pulsed voltage is applied to the emitter assembly; and an outer tube housing the emitter assembly, wherein the outer tube is configured to receive a conductive fluid, wherein the outer tube comprises a distal opening for releasing the plurality of cavitation bubbles or shockwaves and the conductive fluid in a forward direction to treat thrombus at a treatment site.

In some embodiments, when the pulsed voltage is applied across the first wire and the second wire, a current is configured to: flow from the first wire to the conductive sheath to generate a first plurality of cavitation bubbles or shockwaves and, flow from the conductive sheath to the second wire to generate a second plurality of cavitation bubbles or shockwaves.

In some embodiments, the first wire comprises a first exposed distal tip and the second wire comprises a second exposed distal tip.

In some embodiments, the current is configured to flow from the first exposed tip to the conductive sheath and from the conductive sheath to the second exposed tip via a conductive fluid.

In some embodiments, the current is configured to flow from the first exposed distal tip to an inner wall and/or front edge of the conductive sheath.

In some embodiments, the central tube comprises a first segment and a second segment closer to a proximal end of the central tube than the first segment, where the diameter of the second segment is larger than the first segment.

In some embodiments, the second segment comprises a longitudinal groove for accommodating a part of the first insulated wire.

In some embodiments, the curved distal portion of the first wire wraps around the first segment of the central tube.

In some embodiments, the central tube comprises a central lumen for accommodating a guide wire.

In some embodiments, a pump is configured to deliver a continuous flow of conductive fluid to the emitter assembly through the outer tube.

In some embodiments, the conductive fluid comprises saline.

In some embodiments, the continuous flow of conductive fluid flushes debris away from the treatment site.

In some embodiments, the voltage is between 800V and 2700V.

In some embodiments, a repetition rate of the applied voltage pulses is between approximately 4 Hz and 100 Hz.

In some embodiments, the electrode pair comprises a spark gap between electrodes of the pair, the spark gap being less 0.005".

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Described herein are exemplary systems and methods for reducing or removing thrombus from the vascular system of a patient by generating cavitation bubbles and/or shockwaves via a voltage source. In accordance with some embodiments, the treatment system includes a forward firing intravascular catheter that releases cavitation bubbles, shockwaves, or a combination thereof. The catheter comprises a central tube for housing a guidewire, an emitter assembly that can be mounted over the central tube, and an outer tube. In some embodiments, the distal end of the outer tube is open (as opposed to sealed), thus allowing cavitation bubbles and/or shockwaves created by the emitter assembly to be released in a forward direction via the distal opening of the outer tube.

In operation, the catheter can be advanced within the body lumen (e.g., a blood vessel) to the treatment site (e.g., via a guide wire). The emitter assembly includes electrodes that, when connected to pulse generator, form plasma arcs that in turn lead to the generation of shockwaves and/or cavitation bubbles. The cavitation bubbles and/or shockwaves are released in a forward direction via the distal opening of the outer tube. The cavitation bubbles and/or shockwaves create mechanical vibrations, turbulence, jets, and/or forceful collapses to weaken and break the fibrin fiber network, thus reducing and removing thrombus.

In the preferred embodiment, the present invention is essentially a hybrid system combining aspects of both shock wave generation and cavitation bubble generation. The voltage at each emitter (i.e., across the spark gap) can be somewhat lower than conventional intravascular lithotripsy ("IVL"). In addition, the repetition rate is somewhat higher than a typical IVL treatment so as to produce both shock waves and cavitation bubbles. In some embodiments, the catheter can be powered by an 825D generator available from Shockwave Medical, Inc. (IVL Generator Catalog Number IVLGCCD). In some embodiments, the voltage of the generator is adjusted between 1800V and 2700V, and the repetition rate is adjusted to between approximately 4 Hz and 25 Hz. In order to maintain the breakdown voltage, the spark gap at the emitter (e.g., a spark gap formed between two electrodes of an electrode pair) is sufficiently small to allow a spark. In some embodiments, the gap is less than 0.005 inches.

Figure 1A:
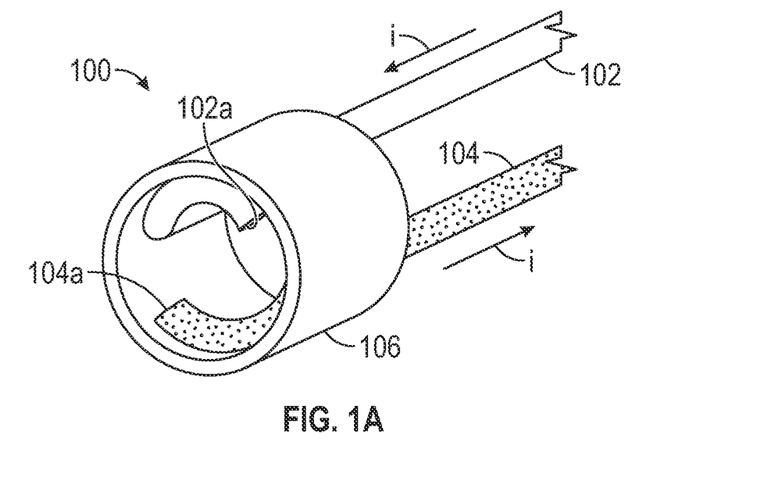
FIG. 1A depicts an exemplary emitter assembly that can be used in a forward firing intravascular catheter, in accordance with some embodiments.

FIG. 1A depicts an exemplary emitter assembly 100 that can be used in a forward firing intravascular catheter, in accordance with some embodiments. The emitter assembly 100 comprises a first wire 102, a second wire 104, and a conductive sheath 106. In some embodiments, the conductive sheath can be stainless steel hypotubes, and the wires can be polyimide-insulated copper wires.

Figure 1B:
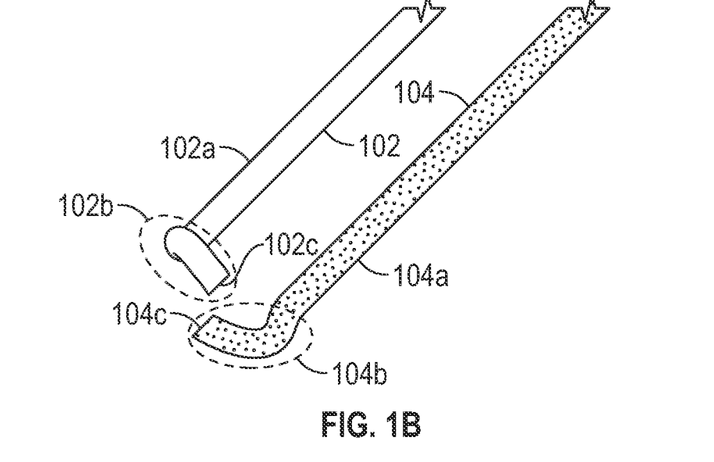
FIG. 1B depicts wires of the exemplary emitter assembly, in accordance with some embodiments.

FIG. 1B provides a perspective view of the wires 102 and 104, in accordance with some embodiments. Wire 102 comprises a straight portion 102a, a curved distal portion 102b, and a conductive distal end 102c. In some embodiments, the conductive distal end 102c is formed by cutting the wires 102 to expose the conductive core under the insulation material. Similarly, wire 104 comprises a straight portion 104a, a curved portion 104b, and a conductive distal end 104c.

Figure 2A:
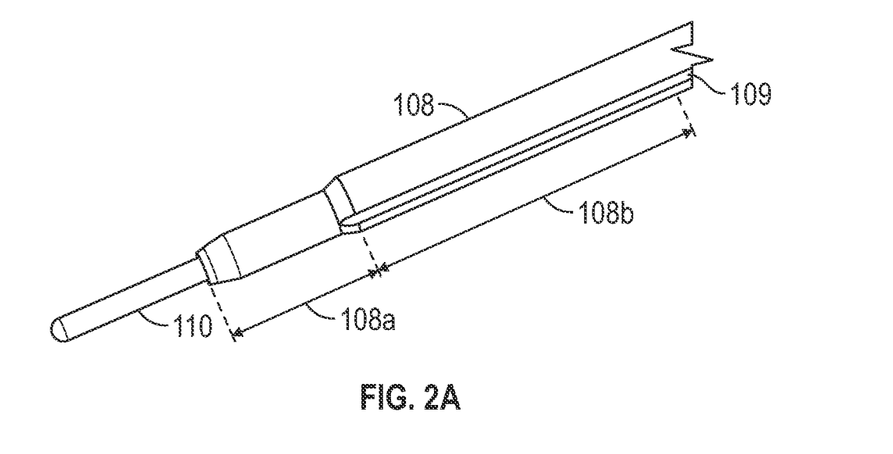
FIG. 2A depicts parts of an exemplary forward firing intravascular catheter, in accordance with some embodiments.

The emitter assembly can be mounted over a central tube within a catheter. With reference to FIG. 2A, an exemplary central tube 108 comprises a central lumen for accommodating a guidewire 110. The central tube further comprises longitudinal grooves (e.g., groove 109) on its outer surface for accommodating wires of the emitter assembly.

In the depicted example in FIG. 2A, the central tube 108 comprises a segment 108a and a segment 108b, where the diameter of the segment 108b is larger than 108a. One or more longitudinal grooves (e.g., groove 109) can be formed over the segment 108b to accommodate wires of the emitter assembly. The deepest point in the groove in segment 108b can be aligned with the outer surface of the segment 108a such that a wire can extend through the groove in the segment 108b and also rest over the segment 108a in a flat or substantially flat manner, as illustrated by wire 104 in FIG. 2B.

Figure 2B:
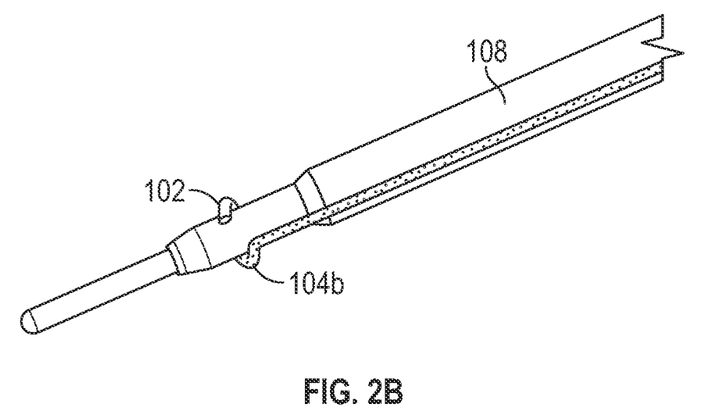
FIG. 2B depicts parts of the exemplary forward firing intravascular catheter, in accordance with some embodiments.
Figure 2C:
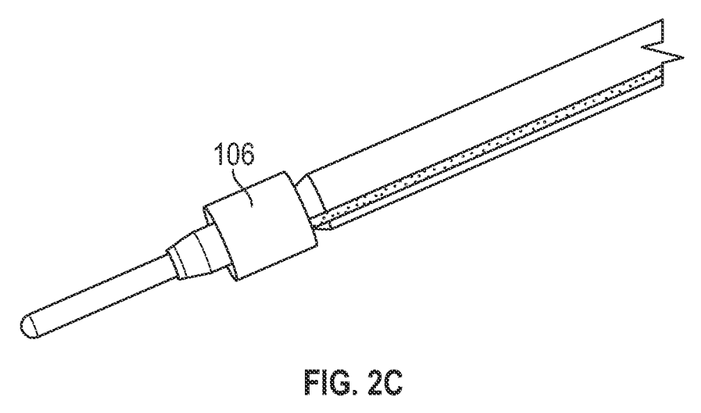
FIG. 2C depicts parts of the exemplary forward firing intravascular catheter, in accordance with some embodiments.

FIGS. 2B and 2C illustrate how an emitter assembly (e.g., the emitter assembly of FIG. 1A) can be mounted over the central tube 108. With reference to FIG. 2B, the wire 104 extends through a longitudinal groove of the central tube 108 and its distal curved portion 104b wraps around the central tube. The wire 102 can be mounted in a similar manner through another longitudinal groove of the central tube 108. The wires can be bonded to the outer surface of the central tube with adhesive (e.g., epoxy or cyanoacrylate adhesive). With reference to FIG. 2C, the conductive sheath 106 of the emitter assembly is placed over (without touching) the distal curved portions of the wires 102 and 104. The conductive sheath 106 can be secured in place with adhesive (e.g., epoxy or cyanoacrylate adhesive). There is a gap between the conductive sheath and each of the distal ends of wires 102 and 104. In some embodiments, the gap is between approximately 0.003" to 0.006".

Figure 2D:
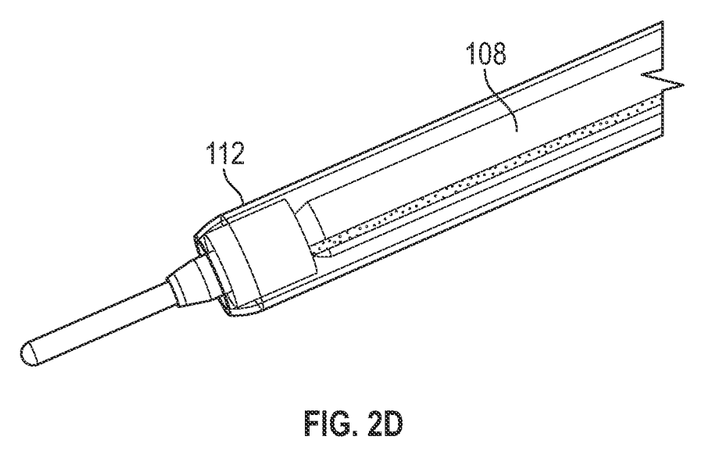
FIG. 2D depicts parts of the exemplary forward firing intravascular catheter, in accordance with some embodiments.

With reference to FIG. 2D, the catheter further comprises an outer tube 112. The outer tube 112 opens at the distal end. As shown, the outer tube 112 wraps around the emitter assembly, including the conductive sheath and the wires. The outer tube can be made of a non-conductive polymer or elastomer (e.g. polyester, polyurethane, polyimide, neoprene, silicone).

Turning back to FIG. 1A, in operation, when the emitter assembly 100 is connected to a voltage source, a current i traverses through the first insulated wire 102, the conductive sheath 106, and the second insulated wire 104 to generate cavitation bubbles and/or shockwaves at two locations. Specifically, the proximal end of the wire 102 is connected to a positive port of a voltage generator (not depicted) and the proximal end of the wire 104 is connected to a negative port of the voltage generator. The generator delivers energy in continuous pulse mode or in the series of short bursts. Accordingly, the current i traverses the emitter assembly as indicated by the arrows. As shown, the current, i, traverses from the proximal end of the wire 102 toward its distal curved portion. At the distal end of the wire 102, the conductive core of the wire is exposed, thus allowing the current to traverse the gap between the distal end of the wire 102 and the conductive sheath 106 (e.g., the inner wall and/or the front edge of the conductive sheath) via a conductive fluid. The exposed distal end of the wire 102 and the conductive sheath 106 form a first electrode pair for generating cavitation bubbles and/or shockwaves.

The current i further traverses the gap between the conductive sheath 106 and the distal end of the second insulated wire 104. At the distal end of the second insulated wire 104, the conductive core of the wire is exposed, thus allowing the current to traverse the gap between the conductive sheath 106 (e.g., the inner wall and/or the front edge of the conductive sheath) and the conductive distal end of the wire 104 via the conductive fluid. The exposed distal end of the second wire 104 and the conductive sheath 106 form a second electrode pair for generating cavitation bubbles and/or shockwaves. The current i then returns to the voltage generator via the second insulated wire 104.

As the current i traverses between a wire and the conductive sheath, a plurality of plasma arcs are formed between the exposed distal end of the wire and the inner wall and/or the front edge of the conductive sheath. Plasma arcs lead to cavitation bubbles and/or shockwaves in a controlled fashion (one at a time, at a particular rate), which in turn lead to mechanical vibrations, and other bubble dynamics-related effects such as collapses, turbulence, jetting, etc. in the conductive fluid (e.g., via the expansion and collapse of the bubbles). The mechanical vibrations serve to reduce or remove the thrombus. Cavitation has been known to weaken the fibrin network crosslink which is the base structure of the thrombus. Combination of mechanical vibrations and bubble cavitation can be effective in thrombolysis.

As shown in FIG. 1A, each of the distal curved portions of the wires 102 and 104 is curved in the same direction as the adjacent inner wall of the conductive sheath 106. In some embodiments, the distal curved portion of each wire can be parallel or substantially parallel to the adjacent inner wall of the conducive sheath. As the plasma arcs cause erosion to the electrodes, each curved portion can erode and shorten over time. Because the curvature of the curved wire portion is similar (e.g., in the same direction) or identical to the curvature of the adjacent inner wall of the conductive sheath, the shortest gap between the distal end of the wire and the conductive sheath can be kept constant or substantially constant, thus ensuring that cavitation bubbles and/or shockwaves are generated in a constant or substantially constant manner. Note that as the curved wire portion erodes, the location of the generation of the cavitation bubbles and/or shockwaves will change. In the illustrated embodiment, the location of the generation of the cavity bubbles and/or shockwaves will rotate circumferentially about the inner periphery of the conductive sheath 106.

As compared to the generators used in the prior art shock wave generation systems mentioned above, the generator for this system may be configured to generate lower-voltage pulses at a higher pulse repetition rate in order to obtain the benefits of both cavitation bubbles and shock waves. For example, in the prior art systems, each pulse might be about 3000 volts with a 1 Hz repetition rate. In embodiments of this system, voltage is adjusted between 800V to 2700V; repetition rate is adjusted to approximately 4 Hz and 100 Hz; pulse duty cycle is adjusted between 20%-60%. These parameters can be varied based on the blood clot condition.

Additional details on electrode pairs formed by a wire and a conductive tube, along with possible variations, are provided in assignee's prior filings U.S. Publication No. 2019/0388110 titled "SYSTEM FOR TREATING OCCLUSIONS IN BODY LUMENS" and U.S. Publication No. 2021/0085348, titled "SYSTEM FOR TREATING THROMBUS IN BODY LUMENS," both of which are incorporated by reference. It should be appreciated that, while FIGS. 1A-2D depict a emitter assembly comprising two wires and a conductive sheath driven by one voltage source, other configurations of emitter assembly can be placed at the distal tip of the catheter to provide forward-firing capabilities.

Figure 3A:
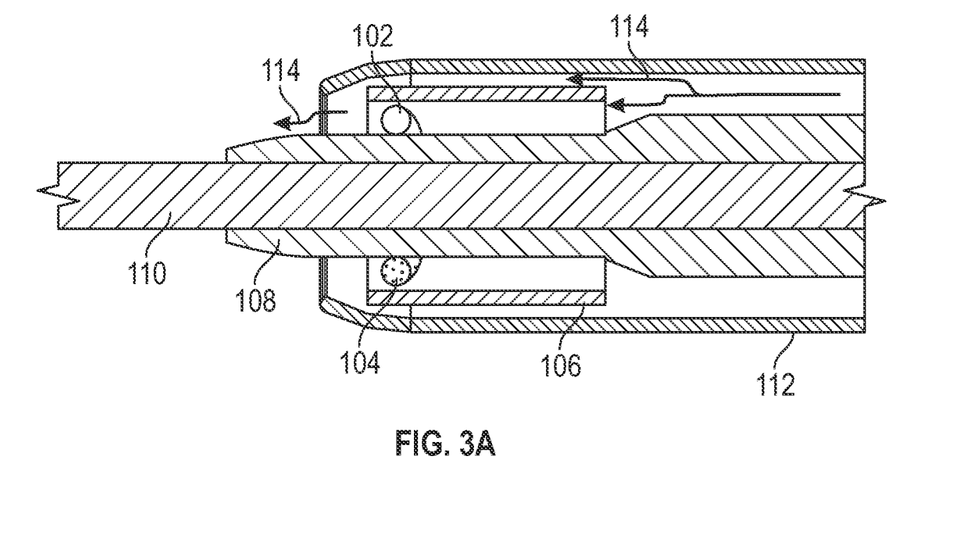
FIG. 3A depicts a cross-sectional view of the distal end of the exemplary forward firing intravascular catheter, in accordance with some embodiments.
Figure 3B:
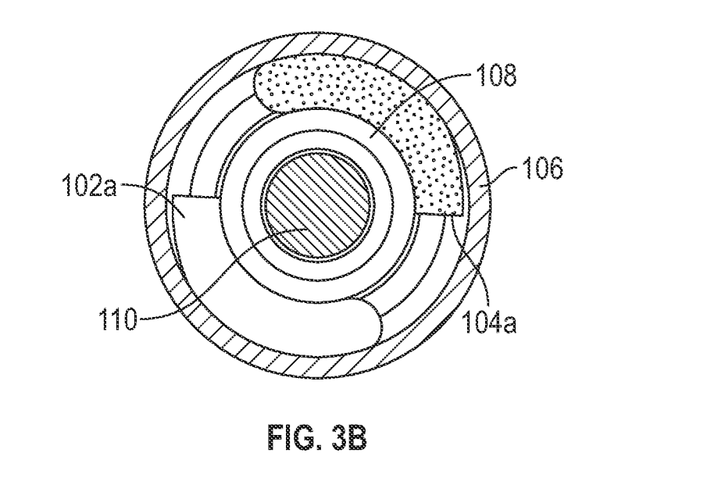
FIG. 3B depicts a front view of the distal end of the exemplary forward firing intravascular catheter, in accordance with some embodiments.

FIGS. 3A and 3B depict a cross-sectional view and a front view of the distal end of the exemplary forward firing intravascular catheter, respectively, in accordance with some embodiments. The central tube 108 comprises a central lumen for accommodating a guidewire 110. An emitter assembly, which comprises wires 102 and 104 and a conductive sheath 106, is mounted over the central tube 108. The emitter assembly comprises two emitters and each emitter comprises an electrode pair. A first electrode pair comprises the distal end of wire 102 and the conductive sheath 106, and a second electrode pair comprises the distal end of the wire 104 and the conductive sheath 106. As seen in FIG. 3B, the curved distal potions have a coiled configuration. Each curved portion extends in a range from about 50 to 120 degrees about the circumference of the first segment 108a of the central tube.

The catheter further comprises an outer tube 112, which wraps around and covers the emitter assembly. In operation, the outer tube 112 is used to deliver an ionic solution (e.g., a conductive solution such as saline or saline mixed with a contrast medium) from a pump to the emitter assembly. When the emitter assembly is connected to a voltage source, plasma arcs are formed via the conductive fluid at each electrode pair (e.g., between the distal end of each wire and the sheath's inner wall and/or the front edge), which in turn lead to a large amount of cavitation bubbles forming and collapsing and/or shockwaves, as described above. The flow of conductive fluid can be continually administered to transport the cavitation bubbles and/or shockwaves forward.

The outer tube 112 has a distal opening for releasing the cavitation bubbles in a forward direction. The electrode pairs are placed close to the distal opening to maximize the release of cavitation bubbles. As indicated by arrows 114 in FIG. 3A, the cavitation bubbles from the emitter assembly are carried out in the forward direction by the pumped flow of the ionic solution through the distal opening to the thrombus. Further, shockwaves are propagated forward through the distal opening. The pumped flow further removes debris (e.g., metals, bubbles) and thrombus fragments from the treatment site. The rapid removal of debris helps to refresh the cavitation. In some embodiments, the pump provides both infusion and aspiration.

The catheter can be used in conjunction with a pump. In some embodiments, the pump delivers an ionic solution (i.e., a conductive solution such as saline or saline mixed with a contrast medium) via the outer tube to the catheter tip where the cavitation takes place. The pump or an auxiliary pump also aspirates debris away from the thrombus region. The infusion flow can be synchronized to the emitter assembly's power delivery to ensure the adequate ionic solution around the emitters. The aspiration flow and infusion flow can be synchronized to maintain the pressure equilibrium at the treatment site. In some examples, the flow of saline or saline/angiographic contrast medium is adjusted to avoid over-heating issues and control treatment efficiency and rate.

In some embodiments, additional components are included in the treatment system, such as a proximal balloon for trapping debris produced by the emitter, a visualization system and/or a steering system for properly navigating (e.g., side branches) and placing the catheter, etc. Additional details of the treatment system are provided in US Publication Nos. 2019/0388110, and 2021/0085348, referenced above and incorporated herein by reference.

In some embodiments, the procedure can take around 30 minutes to an hour, during which the emitter assembly continuously generates cavitation bubbles and/or shockwaves. These operation parameters (e.g., voltage, repetition rate, or pulse duty cycle of the voltage pulses) can be set based on the characteristics of the blood clot (e.g., size of the clot, age of the clot, composition of the clot, softness of the clot, arterial or venous location of the clot, platelet content of the clot, fibrin content of the clot, or some other attribute of the clot) and/or characteristics of the patient (e.g., age or preexisting medical condition of the patient). In some embodiments, after the procedure, a post-operation minimally invasive procedure (e.g., treatment of bleeding, thrombus reforming) can be performed.

It will be understood that the foregoing is only illustrative of the principles of the invention, and that various modifications, alterations and combinations can be made by those skilled in the art without departing from the scope and spirit of the invention. Any of the variations of the various cavitation devices disclosed herein can include features described by any other cavitation devices or combination of shock wave devices herein. Furthermore, any of the methods can be used with any of the cavitation devices disclosed. Accordingly, it is not intended that the invention be limited, except as by the appended claims. For all of the variations described above, the steps of the methods need not be performed sequentially

The invention claimed is:
1. A catheter comprising:
   a central tube;
   an emitter assembly mounted over the central tube, wherein the emitter assembly comprises:
      a conductive sheath;
      a first insulated wire having a first curved distal portion; and
      a second insulated wire having a second curved distal portion,
         wherein the first curved distal portion and the second curved distal portion are positioned within the conductive sheath, and
         wherein the emitter assembly is configured to generate a plurality of cavitation bubbles or shockwaves when a pulsed voltage is applied to the emitter assembly; and
   an outer tube housing the emitter assembly,
      wherein the outer tube is configured to receive a conductive fluid,
      wherein the outer tube comprises a distal opening for releasing the plurality of cavitation bubbles or shockwaves and the conductive fluid in a forward direction to treat thrombus at a treatment site.
2. The catheter of claim 1, wherein, when the pulsed voltage is applied across the first wire and the second wire, a current is configured to:
   flow from the first wire to the conductive sheath to generate a first plurality of cavitation bubbles or shockwaves and,
   flow from the conductive sheath to the second wire to generate a second plurality of cavitation bubbles or shockwaves.
3. The catheter of claim 2, wherein the first wire comprises a first exposed distal tip and the second wire comprises a second exposed distal tip.

4. The catheter of claim 3, wherein the current is configured to flow from the first exposed tip to the conductive sheath and from the conductive sheath to the second exposed tip via a conductive fluid.
5. The catheter of claim 4, wherein the current is configured to flow from the first exposed distal tip to an inner wall and/or front edge of the conductive sheath.
6. The catheter of claim 2, wherein the central tube comprises a first segment and a second segment closer to a proximal end of the central tube than the first segment, where the diameter of the second segment is larger than the first segment.
7. The catheter of claim 6, wherein the second segment comprises a longitudinal groove for accommodating a part of the first insulated wire.
8. The catheter of claim 6, wherein the first curved distal portion of the first wire wraps around the first segment of the central tube.
9. The catheter of claim 1, wherein the central tube comprises a central lumen for accommodating a guide wire.
10. The catheter of claim 1, wherein a pump is configured to deliver a continuous flow of conductive fluid to the emitter assembly through the outer tube.
11. The catheter of claim 10, wherein the conductive fluid comprises saline.
12. The catheter of claim 10, wherein the continuous flow of conductive fluid flushes debris away from the treatment site.
13. The catheter of claim 1, wherein the voltage is between 800V and 2700V.
14. The catheter of claim 1, wherein a repetition rate of the applied voltage pulses is between approximately 4 Hz and 100 Hz.
15. The catheter of claim 1, wherein the emitter assembly comprises a spark gap between the first curved distal portion and the conductive sheath, the spark gap being less than 0.005".
16. The catheter of claim 1 wherein the first and second curved distal portions of the first and second insulated wires have a coiled configuration.
17. The catheter of claim 16 wherein the first and second curved distal portions of the first and second insulated wires extend in a range from about 50 to 120 degrees about the circumference of the central tube.
18. A catheter for treating a thrombus in a blood vessel comprising:
   an elongated central member;
   a first insulated wire extending along the central member, wherein the distal end of the first wire is partially coiled around the distal end of the central member, and wherein the distal tip of the first wire is not insulated;
   a second insulated wire extending along the central member, wherein the distal end of the second wire is partially coiled around the distal end of the central member, and wherein the distal tip of the second wire is not insulated;
   a cylindrical conductive shield positioned around and spaced from the distal ends of the first and second wires; and
   an outer tube surrounding the cylindrical conductive shield and having an open distal end configured so that conductive fluid injected into the proximal end of the outer tube will pass over the distal tips of the first and second wires and be directed out the distal end of the outer tube towards the thrombus and wherein when high voltage pulses are applied across the first and second wires, current will flow along the first wire and jump a first gap between the distal tip of the first wire to the cylindrical conductive shield and then along the cylindrical conductive shield and then jump a second gap between the cylindrical conductive shield and the distal tip of the second wire and back along the second wire to create, at both the first and second gaps, cavitation bubbles or shockwaves that are forwardly directed toward the thrombus.

19. The catheter of claim 18 wherein coiled portions of the first and second wires extend in a range from about 50 to 120 degrees about the circumference of the central member.

20. The catheter of claim 18 wherein the central member includes a lumen for accommodating a guide wire.

21. The catheter of claim 18 wherein the voltage of the high voltage pulses is between 800V and 2700V.

22. The catheter of claim 18, wherein a repetition rate of the applied high voltage pulses is between approximately 4 Hz and 100 Hz.

\* \* \* \* \*